(12) United States Patent
Spencer

(10) Patent No.: US 6,626,846 B2
(45) Date of Patent: Sep. 30, 2003

(54) VENTILATORY CAPACITY METERS

(75) Inventor: David William Spencer, Enfield (GB)

(73) Assignee: Clement Clarke International Ltd., Harlow (GB)

( * ) Notice: Subject to any disclaimer, the term of this patent is extended or adjusted under 35 U.S.C. 154(b) by 0 days.

(21) Appl. No.: 09/964,579

(22) Filed: Sep. 28, 2001

(65) Prior Publication Data

US 2002/0049388 A1 Apr. 25, 2002

(30) Foreign Application Priority Data

Oct. 19, 2000 (GB) .............................................. 0025679

(51) Int. Cl.[7] .................................................. A61B 5/08
(52) U.S. Cl. ........................................ 600/538; 600/544
(58) Field of Search ................................. 600/538, 539, 600/540, 541, 542, 543, 529, 532, 533; 73/23.3, 239, 240, 242, 744

(56) References Cited

U.S. PATENT DOCUMENTS 3,848,585 A    11/1974  Otsap et al.
3,958,565 A  *  5/1976  Wright ........................ 600/540
4,619,134 A  * 10/1986  Bohm et al. .................. 73/1.19
5,672,833 A  *  9/1997  Byerley ..................... 73/861.55

FOREIGN PATENT DOCUMENTS

DE      29721664 U1     5/1998
EP       0727185 A1     8/1996
GB       A-1463814      2/1977

* cited by examiner

Primary Examiner—Max F. Hindenburg
Assistant Examiner—Navin Natnithithadha
(74) Attorney, Agent, or Firm—Jones, Tullar & Cooper, P.C.

(57) ABSTRACT

In a meter for assessing ventilatory capacity, a piston is free of any sliding contact with the body of the meter except over a region which extends axially not less than about 25% of the piston's diameter. In this way, tilting of the piston is avoided. Sliding contact is further reduced by the piston or wall having contact ribs extending axially.

11 Claims, 3 Drawing Sheets

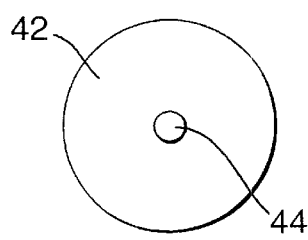
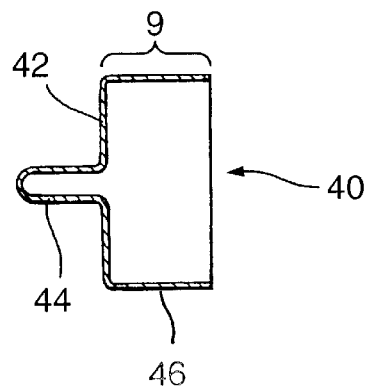
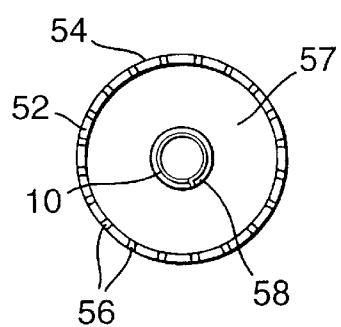
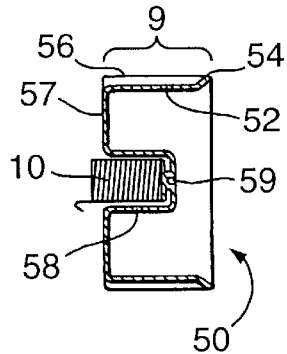
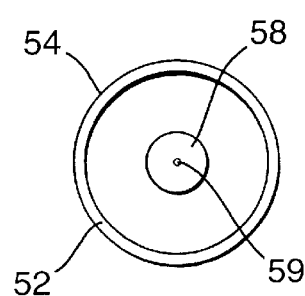
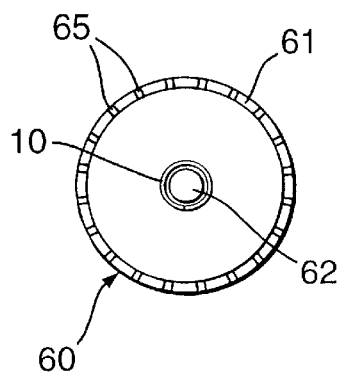
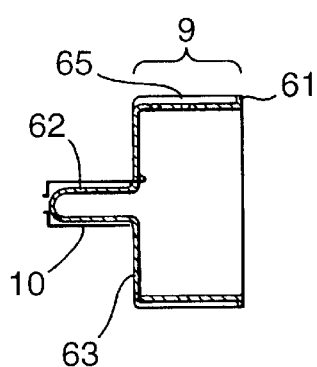
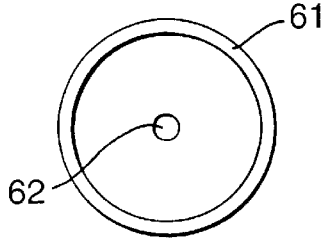

US 6,626,846 B2

VENTILATORY CAPACITY METERS

TECHNICAL FIELD

This invention relates to meters for measuring the ventilatory capacity of a subject, particularly, but not necessarily exclusively the exhalation capacity.

Meters for obtaining a measure of the peak flow rate of exhalation are known (GB-A-1463814) in which the subject blows into one end of a tubular body to displace a piston, against the force of a spring, along the body. The piston is guided slidably for this displacement, out of contact with the body inner wall, on a support rod extending along the axis of the tube. The tube has an open slot running in the direction of piston displacement which provides an exit opening for the air being blown in. A pointer located behind the piston has a light frictional engagement with the slot and is displaced along a scale by the piston as it moves forward against the spring force. The piston is drawn back by the spring when the intensity of exhalation falls, but when it moves back, the pointer remains at the position of maximum displacement of the piston, so giving an indication of the maximum flow rate obtained in the exhalation.

Such meters have been developed as reliable and robust instruments. However, the presence of the central support rod for guiding the piston complicates the assembly process.

BACKGROUND ART

In one of its aspects, the present invention provides a meter for measuring the ventilatory capacity of a subject, the meter comprising a chamber, a piston within the chamber being displaceable axially against a resilient bias by blowing air into the chamber, an exit slot located in a side of the chamber for the escape of the air from the chamber being increasingly opened by the displacement of the piston against the bias, there being a region of sliding contact between the piston and the chamber inner wall at any one position of the piston and the sliding contact region having bounds separated axially by a distance not substantially less than 25% of the transverse dimension of the piston, preferably at least 30%, the sliding contact guiding the movement of the piston and preventing tilting of the piston, and there being means for recording a maximum displacement of the piston. Preferably the axial extent of the periphery is 50% or more of the transverse dimension of the piston, i.e. for a cylindrical piston, its diameter.

By giving the contact region a sufficient axial extent it is possible to avoid the need to mount the piston on a support rod, i.e. the piston is a free piston. The assembly of the meter is simplified and its construction costs reduced.

The piston periphery may take the form of a cylindrical wall of complementary form to and in sliding contact with the chamber inner wall. However, while such a configuration can prevent tilting of the piston, it can affect adversely the accuracy and repeatability of the meter, particularly at low levels of air flow. One reason for this may be that in use, condensation or other matter may be deposited from the exhalations and can accumulate on the periphery of the piston.

These effects could be lessened by increasing the nominal clearance between the piston and the chamber wall. However, the piston is then more likely to tilt and possibly jam within the chamber. The problem can be solved by making the contact between piston and the inner wall peripherally discontinuous e.g. by the provision of ribs on the piston or on the wall: thus the contact area is lessened but resistance to tilting can be maintained.

According to another aspect of the invention a meter for measuring the ventilatory capacity of a subject comprises a chamber, a piston within the chamber displaceable against a resilient bias by blowing air into the chamber, an exit slot located in a side of the chamber for the escape of the air from the chamber being increasingly opened by the displacement of the piston against the bias, portions supporting the piston on the chamber wall against tilting and arranged to engage between the piston and the chamber wall over only a part of the axial and/or circumferential extent of the periphery of the piston; and means for recording a maximum displacement of the piston in the chamber. Thus the piston may be a free piston, i.e. be one devoid of support except from the chamber wall.

Thus, the contact region can comprise a plain, e.g. cylindrical, wall or a plurality of axially spaced peripheral rims. At least one of the peripheral rims may have a complementary profile to the internal cross-sectional form of the chamber. Alternatively, the region can comprise a plurality of circumferentially spaced axially extending ribs. In another form, an axially restricted disc of a piston is complemented by a plurality of ribs forming axial extensions increasing the axial contact length between the piston and the chamber wall.

In these and similar forms of piston, as well as in the case in which the piston has a cylindrical wall, the co-acting wall of the chamber may be formed so that there is contact only at angularly spaced regions. For example, a circular piston may be mounted in a chamber which has a non-circular cross-section or a non-circular piston mounted in a circular cross-section chamber. Alternatively, the chamber may have inwardly extending projections for slidably guiding the piston.

The resilient bias acting on the piston should be applied in a manner that does not produce any significant non-axial force that might cause the piston to tend to tilt. If a coil spring is employed as the biasing device, it is therefore preferably attached centrally to the piston.

BRIEF DESCRIPTION OF THE DRAWINGS

By way of example, embodiments of the invention will be described with reference to the accompanying drawings, in which:

FIGS. 6 and 7 are respectively front and sectioned side views of an alternative piston for use with the meter of FIGS. 1 and 2;

FIGS. 9 and 10; 11, 12 and 13,; and 14, 15 and 16 are respective front, sectioned side, and rear views of three further pistons for use with the meter of FIGS. 1 and 2;

DESCRIPTION OF THE PREFERRED EMBODIMENTS

Figure 1:
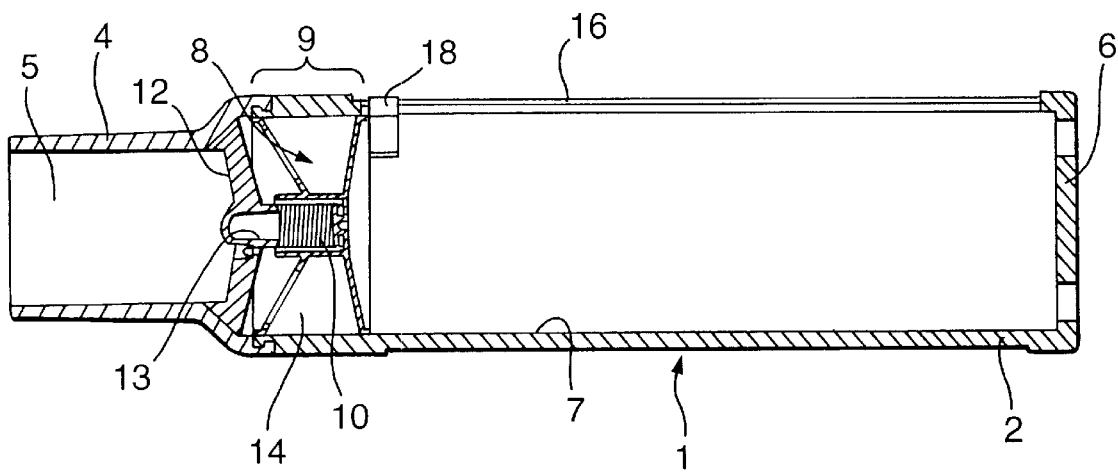
FIG. 1 is a section through a peak flow meter embodying the present invention with a piston in a first position.
Figure 2:
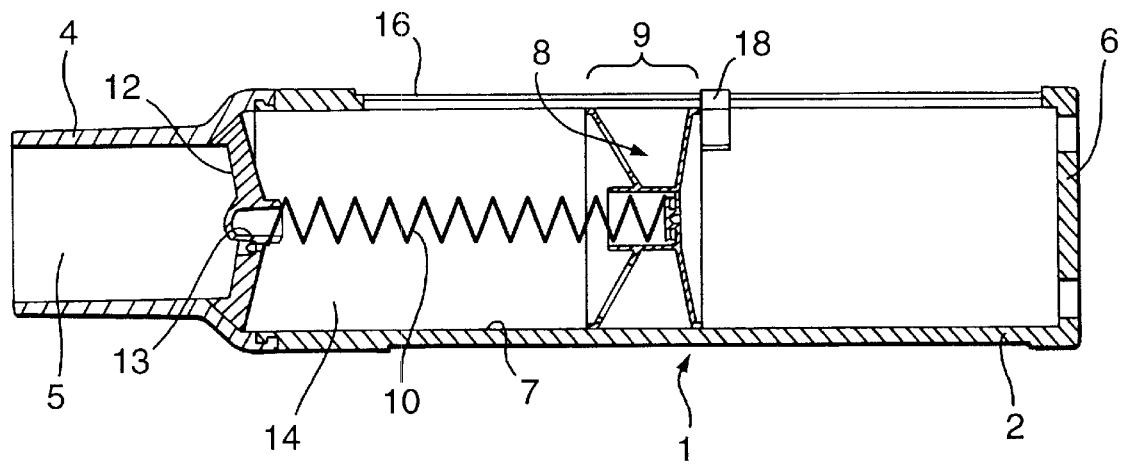
FIG. 2 is a section through a peak flow meter embodying the present invention with a piston in a second position.

The meter 1 shown in FIGS. 1 and 2 comprises a hollow cylindrical body 2 having an inlet end 4 and an apertured closure member 6 at its opposite end. A generally circular-periphery floating piston 8 dividing the chamber formed by the interior of the body is freely movable along the body with sliding contact with the inner surface 7 of its wall. The piston 8 is attached by a coil tension spring 10 to a spider-like retainer member 12 mounted within the inlet end 4, to which it is drawn by the spring 10 to lie in the rest position shown in FIG. 1.

When a subject blows into the inlet end 4, air flows through inlet passage 5 into the void 14 between the retainer member 12 and a disc of the piston 8 and the air pressure drives the piston 8 away from the retainer 12, e.g. to the position shown in FIG. 2. As the piston moves along the body 2 of the meter, it progressively uncovers a longitudinal slot 16 in the body wall through which the flow can escape. A pointer 18 is mounted in the slot and has a light frictional engagement with its edges. The displacement of the piston 8 away from the retainer member 12 entrains the pointer 18 along the slot but the pointer 18 is not attached to the piston 8. Thus, when the pressure in the chamber 14 falls as the rate of exhalation through the mouthpiece 4 decreases, the spring 10 draws the piston 8 back but the pointer 18 is retained frictionally at the position of maximum piston displacement. A scale (not shown) along the slot 16 then allows the peak exhalatory flow to be read off.

The mode of operation described is similar to that of known peak flow meters of the form described in GB-A-1463814. However, the structure of the embodiment and particularly of its piston, and the relationship of the latter to the inner wall of the body, are quite different.

Figure 3:
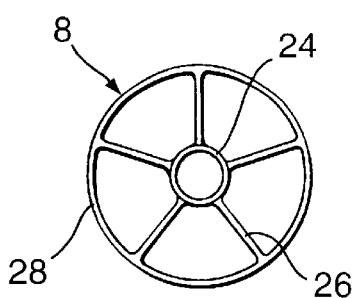
FIGS. 3, 4 and 5 are respectively front, sectioned side, and rear views of the piston of the meter of FIGS. 1 and 2.
Figure 4:
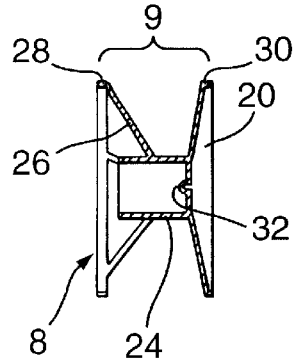
Figure 5:
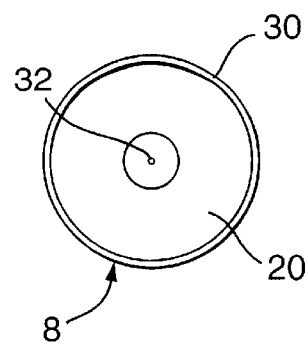

The piston 8, which is shown also in FIGS. 3–5, comprises a frustoconical disc 20 extending from a hollow cylindrical hub 24. Spokes 26 projecting from the hub 24 support a steadying rim 28 having substantially the same outer diameter as a rim 30 at the periphery of the disc 20. The disc and steadying rims 30,28 provide two coaxial support surfaces at a spacing of approximately 50% of the piston diameter which engage the body wall to guide the piston 8 as it slides and to prevent it from tilting, while the disc 20 limits flow past the piston 8.

The hub 24 has, at its inner end, a central pip 32 engaging one end of the spring 10 which is thereby attached centrally to the disc 20. At the other end the spring 10 is attached to a central hub 13 of the retainer member 12, so the force exerted by the spring 10 on the piston 8 does not tend to apply a torque to the piston. By virtue of the axial distance between the bounds of the region 9 of contact between the wall and the piston, here are represented by the rims 28 and 30, which should amount to not substantially less than 25% of the diameter of the piston, preferably 30% or more, any tilting moments which may occur do not significantly tilt the free piston and therefore do not have any significant detrimental effect on the freedom of movement of the piston.

The piston 8 is arranged in the body 2 of the meter with the disc 20 further from the inlet end of the meter, but it is also possible to arrange the disc and spokes in the reverse orientation, with the disc 20 nearer the inlet end. In either case, as the piston 8 slides along the body 2 against the spring bias, the outer periphery of the downstream end of the piston drives the pointer 18 along the slot 16 to mark the peak flow position.

The piston 40 of FIGS. 6 and 7, which can be used instead of the piston 8 shown in FIGS. 1–5, is generally cup-shaped, comprising an end disc 42 with a spigot 44 projecting axially from its base for connection of the spring 10. Projecting in the opposite axial direction from the periphery of the end disc 42 is an annular skirt 46. The plain cylindrical outer surface of the skirt 46 is in sliding engagement with the wall of the body 2, and since at any one time it extends over an axial length 9 which is at least 25% of the piston diameter prevents the piston 40 from tilting within the body. This form of piston is, however, suitable only for applications in which the accuracy and repeatability are less critical, as the large sliding contact area makes it susceptible to variations of performance.

FIGS. 8–16 show other alternative pistons that can be used in the meter of FIGS. 1 and 2. All of these pistons are generally cup-shaped, having a closure element in the form of a disc and a skirt extending axially from the disc providing guidance means to counter tilting forces.

The piston 50 of FIGS. 8–10 has a cylindrical skirt 52 with a flared peripheral lip 54, the outer edge of the lip providing sliding contact with the body 2 of the meter. A series of ribs 56 extend from the lip 54 along the skirt 52 from which they protrude radially to the same diameter as the outer periphery of the lip 54. The ribs are equally spaced around the skirt and extend parallel to the axis of the piston 50. Together, the ribs 56 and the peripheral lip 54 guide the piston and support it against tilting in the body. A base 57 of the cup provides the reaction face by which exhaled air entering from the inlet 4 drives the piston in the chamber against spring 10.

As in the first example, a central pocket 58 is provided in the upstream side with a pip 59 giving a central connection for the spring 10.

FIGS. 11–13 illustrate some possible modifications of the piston of FIGS. 8–10. In piston 60 a peripheral lip 61 extends perpendicular to the axis of movement and together with ribs 65 is for sliding contact with the body. In place of the pocket 58, a spigot 62 with a diameter close to the inner diameter of the spring 10 projects from the base 63 of the piston for attaching and supporting the spring.

Figure 14:
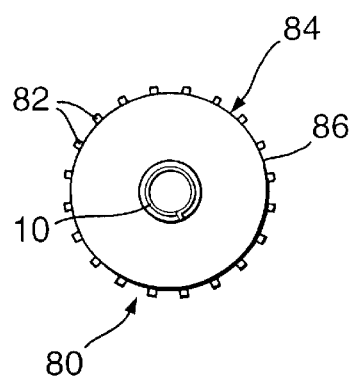
Figure 15:
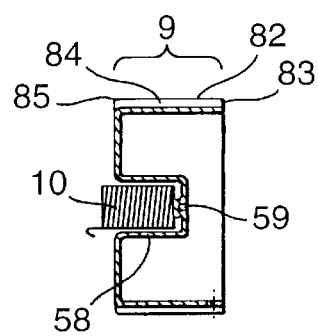
Figure 16:
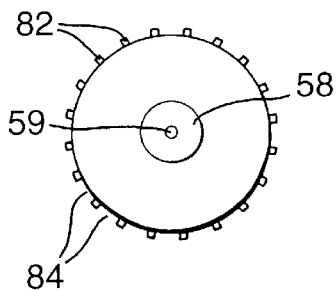

FIGS. 14–16 show a piston 80 which has a series of ribs 82 similar to the pistons 50 and 60, but the spaces 84 between the ribs 82 are not closed by a peripherally projecting lip such as lips 54 or 61. Thus, through slots are formed between the ribs 82 allowing a leakage air flow past the piston 80. The radially outer edges of the ribs 82 guide and support the piston as it slides in the body of the meter.

In all of these embodiments, the axial bounds (lip 54 or 61 plus ribs 56 or 65, or ribs 82) of the contact region 9 between the piston and the wall of the chamber is at least 25% of the diameter of the piston, for the reasons explained previously.

Figure 17:
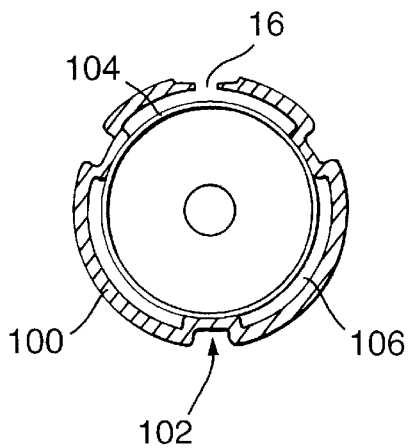
FIG. 17 is a cross-section through a second peak flow meter embodying the invention.
Figure 18:
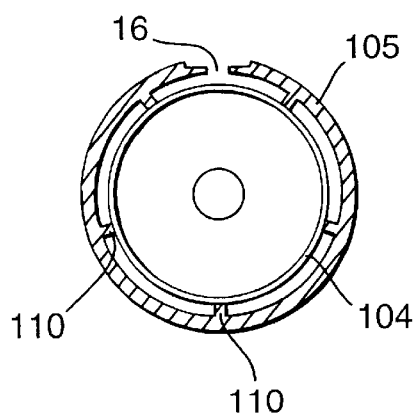
FIG. 18 is a cross-section illustrating a modification of the body of the meter of FIG. 17.

FIGS. 17 and 18 show how meters embodying the present invention may provide ribs on the inner surface of the body to achieve limited contact between piston and body.

In FIG. 17 the body wall 100 of the meter which otherwise is as in FIGS. 1 and 2 is shaped to form three radially inwardly projecting broad ridges 102, providing equally spaced inner surfaces in sliding contact with a cylindrical piston such as piston 8 or piston 40 to guide and support it as it slides along the body. The ridges 102 extend along the body so as to support the piston through its complete range of movement. Between the ridges 102, spaces 106 are formed between the piston 104 and the body inner wall which allow a leakage air flow around the piston.

FIG. 18 shows a similar arrangement using a series of relatively narrow longitudinal ribs 110 projecting inwardly to act as the contact area of the piston 104 with the inner surface of the body wall 100.

In these modifications, the axial bounds of the contact zone between the piston and the wall are as before spaced apart by at least 25% of the diameter of the piston.

It will be understood that although the illustrated examples have been related to a known form of meter, the invention is capable of wider application to other forms of ventilatory capacity meters which rely on the displacement of a piston in a chamber.

What is claimed is:

1. A meter for measuring the ventilatory capacity of a subject, the meter having: a chamber formed by a wall with an axial direction defined by an inner surface of said wall, said chamber having an exit slot in said wall; a piston within said chamber being displaceable axially against a resilient bias by blowing air into said chamber, and means for recording a maximum displacement of said piston, said piston having a transverse dimension perpendicular to said axial direction, said exit slot being adapted for the escape of the air from said chamber as said slot is increasingly opened by the displacement of said piston against said bias, there being a bounded region of a sliding contact between said piston and said inner surface of said wall of at any one position of said piston, said bounded region being separated axially by a distance not less than about 25% of the transverse dimension of said piston, said sliding contact guiding displacement of said piston and preventing tilting of said piston.

2. A meter according to claim 1, wherein said distance is not less than about 30% of the transverse dimension of said piston.

3. A meter according to claim 1, wherein said piston is free of other sliding contact during its displacement.

4. A meter according to claim 3, wherein said bounds are respective support rims of said piston.

5. A meter according to claim 2, wherein said piston makes peripherally at least partly discontinuous contact with said inner surface of said wall.

6. A meter according to claim 5, wherein said piston has axially extending, peripherally spaced-apart, ribs for making sliding contact with said inner surface of said wall.

7. A meter according to claim 6, wherein said piston additionally has a peripherally continuous lip at one axial end for making contact with said inner surface of said wall.

8. A meter according to claim 5, wherein said piston makes only peripherally discontinuous contact with said inner surface of said wall over the whole of its axial length.

9. A meter according to claim 8, wherein contact between said piston and said inner surface of said wall is provided by axially-extending, inward projections of said inner surface of said wall.

10. A meter for measuring the ventilatory capacity of a subject, the meter having: a chamber formed by a wall with an axial direction defined by an inner surface of said wall, said chamber having a exit slot in said wall; a piston within said chamber being displaceable axially against a resilient bias by blowing air into said chamber, and means for recording a maximum displacement of said piston, said piston having a transverse dimension perpendicular to said axial direction, said exit slot being adapted for the escape of the air from said chamber as said slot is increasingly opened by the displacement of said piston against said bias, wherein sliding contact between said piston and said inner surface of said wall being at any one time at least at positions spaced axially apart by not less than about 25% of the transverse dimension of said piston, said sliding contact guiding displacement of said piston and preventing tilting of said piston.

11. A meter according to claim 10, wherein said piston is guided in said chamber only by said sliding contact with said inner surface of said wall.

* * * * *